United States Patent
Boaz

(10) Patent No.: US 9,695,110 B2
(45) Date of Patent: Jul. 4, 2017

(54) REDUCTIVE PREPARATION OF TERTIARY DIMETHYLAMINES FROM NITRILES

(71) Applicant: Eastman Chemical Company, Kingsport, TN (US)

(72) Inventor: Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 75 days.

(21) Appl. No.: 14/745,508

(22) Filed: Jun. 22, 2015

(65) Prior Publication Data

US 2016/0368856 A1  Dec. 22, 2016

(51) Int. Cl.
*C07C 209/48* (2006.01)
*C07C 213/02* (2006.01)

(52) U.S. Cl.
CPC .......... *C07C 209/48* (2013.01); *C07C 213/02* (2013.01)

(58) Field of Classification Search
CPC ............................ C07C 209/48; C07C 213/02
See application file for complete search history.

(56) References Cited

U.S. PATENT DOCUMENTS

| | | |
|---|---|---|
| 5,237,088 A | 8/1993 | Weigert |
| 5,463,130 A | 10/1995 | Witzel et al. |
| 5,557,011 A | 9/1996 | Witzel et al. |
| 5,869,653 A | 2/1999 | Johnson |
| 5,894,074 A * | 4/1999 | Fuchs .................. C07C 213/02 564/490 |
| 7,709,655 B2 | 5/2010 | Zhang |

FOREIGN PATENT DOCUMENTS

| | | |
|---|---|---|
| EP | 1 094 058 A1 | 4/2001 |
| WO | WO 2013/169401 A1 | 11/2013 |

OTHER PUBLICATIONS

Handbook of Chemistry and Physics, 97th Print Edition, 2016, pp. 5-88 to 5-97.*
Chen et al.; "Hydrogen transfer reduction of nitriles in DBU based ionic liquids"; ARKIVOC; 2012; (viii); pp. 128-136.
Gowda et al.; "Application of hydrazinium monoformate as new hydrogen donor with Raney nickel: a facile reduction of nitro and nitrile moieties"; Tetrahedron; 58; (2002); pp. 2211-2213.
Mebane et al.; "Transfer Hydrogenation of Nitriles with 2-Propanol and Raney® Nickel"; Synthetic Communications: An International Journal for Rapid Communication of Synthetic Organic Chemistry; vol. 33, No. 19, pp. 3373-3379, 2003.
Moiseev et al.; "Facile hydrogen-transfer reduction of multiple bonds by formic acid catalyzed with a Pd-561 giant cluster"; Mendeleev Commun.; 1997; 7(1); pp. 1-3.
Shares et al.; "An efficient synthesis of tertiary amines from nitriles in aprotic solvents"; Tetrahedron Letters; 53(2012); pp. 4426-4428.
Copending U.S. Appl. No. 14/745,506, filed Jun. 22, 2015, Neil Warren Boaz.
Yap, Jeanette See Leng, et al.; "Synthesis, Optical Resolution, and Stereochemical Properties of a Rationally Designed Chiral C-N Palladacycle"; Organometallics, 33(4), 930-940, 2014.
Stutz, Anton, et al.; "Synthesis and Structure-Activity Relationships of Naftifine-Related Allylamine Antimycotics"; J. Med. Chem., 1986, 29(1), 112-125.
Sorribes, Ivan, et al.; "Direct Catalytic N-Alkylation of Amines with Carboxylic Acids"; Journal of the American Chemical Society, vol. 136, No. 40, pp. 14314-14319, 2014.
Periasamy, Mariappan, et al.; "Methods of enhancement of reactivity and selectivity of sodium borohydride for applications in organic synthesis"; Journal of Organometallic Chemistry, 609, (2000), pp. 137-151.
Ram, Siya, et al.; "Ammonium Formate in Organic Synthesis: A Versatile Agent in Catalytic Hydrogen Transfer Reductions"; Synthesis, Georg Thieme Verlag, Stuttgart, DE, 1998, pp. 91-95, XP001183863.
Notification of Transmittal of the International Search Report and The Written Opinion of the International Searching Authority, or the Declaration, International Application No. PCT/US2016/036577 with a filed of Jun. 9, 2016.
Notification of Transmittal of The International Search Report and The Written Opinion of the International Searching Authority, or the Declaration, International Application No. PCT/US2016/036600 with a filing date of Jun. 9, 2016.
Ikawa, Takashi, et al.; "Selective N-alkylation of amines using nitriles under hydrogenation conditions: facile synthesis of secondary and tertiary amines"; Org. Biomol. Chem., 2012, vol. 10, pp. 293-304.
USPTO Notice of Allowance for U.S. Appl. No. 14/745,506 dated Jun. 29, 2016.

* cited by examiner

*Primary Examiner* — Paul A Zucker
*Assistant Examiner* — Mark Luderer
(74) *Attorney, Agent, or Firm* — Kenrick L. Vidale

(57) ABSTRACT

This disclosure describes a low temperature process for the preparation of dimethyl amines from nitriles via reductive amination. In some embodiments, the process proceeds under mild conditions with aqeuous dimethylamine and show an unexpected rate acceleration by the inclusion of an acid addition salt of the dimethylamine.

28 Claims, No Drawings

REDUCTIVE PREPARATION OF TERTIARY DIMETHYLAMINES FROM NITRILES

BACKGROUND

Reductive amination of nitriles in the presence of a secondary amine is a known process for preparing tertiary amines from nitriles. These reductions are generally run at high temperatures and pressures, and often result in poor selectivity, low conversions, or high secondary amine loading. The preparation of tertiary dimethylamines by the reductive amination of aliphatic nitriles with dimethylamine using heterogeneous catalysts has been explored. These reactions generally use liquid (anhydrous) dimethylamine and are performed at high temperatures (at or above 120° C.) and high pressures (80-200 bar or 8-20 MPa). The catalysts for these reductions are usually either palladium on a support or Raney nickel. In the latter case an improvement of the reaction was observed with inclusion of a catalytic amount of a hydroxide base, either in the catalyst preparation or in the reaction mixture itself. The use of high pressures for these hydrogenations requires expensive pressure-rated vessels and expensive and dangerous high pressure compressed hydrogen. The use of high temperature in these reactions can afford increased color (amines tend to discolor at high temperature) and reduced reaction selectivity due to side reactions of the starting materials or products. For example, substrates such as 3-hydroxypropionitrile or 3-dimethylaminopropionitrile may be prone to elimination reactions to afford acrylonitrile at elevated temperatures, which would lead to reduced yields of the desired products and contamination with side products from the acrylonitrile, necessitating significant product purification.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

An embodiment concerns a method of the preparation of tertiary dimethylamines by the reductive amination of a nitrile. In some embodiments, the method may be carried out in the presence of at least one catalyst, dimethylamine, and a dimethylammonium acid addition salt. In some embodiments, the method may be carried out in an atmosphere containing hydrogen.

DETAILED DESCRIPTION

This disclosure describes a method for the preparation of tertiary dimethylamines by the reductive amination of nitriles under mild conditions of temperature and pressure. Such a method uses less energy, require less expensive reaction vessels, and avoid decompositions issues that are often prevalent at high temperatures.

In some embodiments, this disclosure describes a method for the preparation of tertiary dimethylamines represented by the general formula 1 by the reductive amination of nitriles represented by general formula 2:

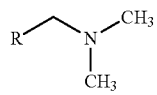

1

2 wherein R is selected from substituted and unsubstituted, branched- and straight-chain $C_1$-$C_{22}$ alkyl, substituted and unsubstituted $C_3$-$C_8$ cycloalkyl, substituted and unsubstituted $C_6$-$C_{20}$ carbocyclic aryl, and substituted and unsubstituted $C_1$-$C_{20}$ heterocyclic wherein the heteroatoms are selected from sulfur, nitrogen, and oxygen, or mixtures thereof, wherein the hydrogenation is carried out in the presence of a catalyst, dimethylamine, and a soluble dimethylammonium acid addition salt.

The branched- and straight-chain $C_1$-$C_{22}$ alkyl groups which may be represented by R may be straight- or branched-chain hydrocarbon radicals containing up to about 22 carbon atoms and may be substituted, for example, with one to three groups selected from $C_1$-$C_6$ alkoxy, $C_2$-$C_6$ alkoxycarbonyl, $C_2$-$C_6$ alkanoyloxy, hydroxy, $C_2$-$C_{10}$ dialkylamino, carbocyclic aryl, and heterocyclic. The terms "$C_1$-$C_6$ alkoxy", "$C_2$-$C_6$ alkoxycarbonyl", and "$C_2$-$C_6$ alkanoyloxy" are used to denote radicals corresponding to the structures —$OR^1$, —$CO_2R^1$, and —$OCOR^1$, respectively, wherein $R^1$ is $C_1$-$C_6$ alkyl or substituted $C_1$-$C_6$ alkyl.

The $C_3$-$C_8$ cycloalkyl groups which may be represented by R may be a saturated, carbocyclic hydrocarbon radical having three to eight carbon atoms and may be substituted, for example, with one to three groups selected from $C_1$-$C_6$ alkoxy, $C_2$-$C_6$ alkoxycarbonyl, $C_2$-$C_6$ alkanoyloxy, hydroxy, $C_2$-$C_{10}$ dialkylamino, carbocyclic aryl, and heterocyclic. The terms "$C_1$-$C_6$ alkoxy", "$C_2$-$C_6$ alkoxycarbonyl", and "$C_2$-$C_6$ alkanoyloxy" are used to denote radicals corresponding to the structures —$OR^1$, —$CO_2R^1$, and —$OCOR^1$, respectively, wherein $R^1$ is $C_1$-$C_6$ alkyl or substituted $C_1$-$C_6$ alkyl.

The carbocyclic aryl groups which R or any substituent may represent may include phenyl, naphthyl, or anthracenyl and phenyl, naphthyl, or anthracenyl substituted with one to three substituents selected from $C_1$-$C_6$ alkyl, substituted $C_1$-$C_6$ alkyl, hydroxy, $C_2$-$C_{10}$ dialkylamino, $C_6$-$C_{10}$ aryl, substituted $C_6$-$C_{10}$ aryl, $C_1$-$C_6$ alkoxy, halogen, carboxy, $C_1$-$C_6$ alkanoyloxy, $C_1$-$C_6$ alkylsulfonyl, trifluoromethyl, $C_2$-$C_6$ alkoxycarbonyl, $C_2$-$C_6$ alkanoylamino and O—$R^2$, —$SO_2$—$R^2$, —$NHSO_2R^2$ and —$NHCO_2R^2$, wherein $R^2$ is phenyl, naphthyl, or phenyl or naphthlyl substituted with one to three groups selected from $C_1$-$C_6$ alkyl, $C_6$-$C_{10}$ aryl, and $C_1$-$C_6$ alkoxy.

The heterocyclic radicals which R or any substituent may represent may include a 5- or 6-membered aromatic ring containing one to four heteroatoms selected from oxygen, sulfur and nitrogen. Examples of such heterocyclic radicals are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heterocyclic radicals may be substituted, for example, with up to three groups such as $C_1$-$C_6$ alkyl, $C_1$-$C_6$ alkoxy, substituted $C_1$-$C_6$ alkyl, hydroxy, $C_2$-$C_{10}$ dialkylamino, aryl, aryloxy, $C_2$-$C_6$ alkoxycarbonyl and $C_2$-$C_6$ alkanoylamino. The heterocyclic radicals also may be substituted with a fused ring system, e.g., a benzo or naphtho residue, which may be unsubstituted or substituted, for example, with up to three of the groups set forth in the preceding sentence.

In some embodiments, the compounds of the invention are exemplified by formula 1 wherein R is a branched- and straight-chain, saturated $C_1$-$C_{22}$ alkyl or a hydroxy-substituted branched- and straight-chain, saturated $C_1$-$C_{22}$ alkyl or a dialkylamino-substituted branched- and straight-chain, saturated $C_1$-$C_{22}$ alkyl or a carbocyclic aryl or substituted carbocyclic aryl. In some embodiments, the compounds of the invention are further exemplified by formula 1 wherein R is ethyl, 2-hydroxyethyl, 2-dimethylaminoethyl, or phenyl.

In some embodiments, the method comprises the hydrogenation of nitrile 2 in the presence of a catalyst, dimethylamine, and a soluble dimethylammonium salt.

The process may be carried out at a temperature between from about −100° C. to about +200° C., from about 0° C. to about 150° C., or from about 20° C. to about 100° C. In some embodiments, the method may be carried out at a temperature less than about 150° C. or less than about 100° C.

The catalyst may be chosen from Group VIII metals. In some embodiments, Group VIII metals may include palladium and platinum. The Group VIII metals may be on a support, which can be chosen from carbon, alumina, silica, and the like. In some embodiments, the weight percent loading of the metal on the support can be from about 0.25% to about 20%, or from about 0.5% to about 10%, or from about 1% to about 7.5%. The amount of supported catalyst can vary from about 1 to about 50 weight percent based on the weight of substrate 2, or from about 2% to about 25%, or from about 4% to about 15%.

The amount of dimethylamine may be from about 0 to about 20 equivalents based on nitrile 2, from about 0 to about 5 equivalents, or from about 0 to about 2 equivalents. In some embodiments, the dimethylamine can be an aqueous solution with a dimethylamine content from about 10% to about 90%, from about 20% to about 80%, or from about 30% to about 70%.

The dimethylammonium salt may be any addition salt that is soluble in the reaction mixture. These salts can be pre-prepared and isolated or can be prepared in situ from dimethylamine and an acid. Acids used to form the dimethylammonium salt (isolated or in situ) are protic acids with a pKa of <5, and can include acetic acid, benzoic acid, propionic acid, hydrochloric acid, sulfuric acid, methanesulfonic acid, phosphoric acid, formic acid, citric acid and the like. Examples of the dimethylammonium salts include dimethylammonium acetate, dimethylammonium chloride (also known as dimethylamine hydrochloride), and dimethylammonium sulfate. In some embodiments, the amount of dimethylammonium salt can be from about 0.01 to about 20 equivalents based on nitrile 2, from about 0.1 to about 5 equivalents, or from about 0.2 to about 2 equivalents.

In some embodiments, the reaction may be performed under an atmosphere that contains hydrogen. The pressure of the reaction can be from about 1 atmosphere to about 150 atmospheres (from about 0.1 to about 15.2 MPa), from about 1 atmosphere to about 70 atmospheres (from about 0.1 to about 7.1 MPa), from about 1 atmosphere to about 35 atmospheres (from about 0.1 to about 3.55 MPa), from about 1 atmosphere to about 10 atmospheres (from about 0.1 to about 1.01 MPa), or from about 1 atmosphere to about 5 atmospheres (from about 0.1 to about 0.51 MPa).

In some embodiments, the reaction may be performed in an inert solvent in addition to any solvent that may be introduced with a reagent (for example, the water content in a dimethylamine aqueous solution). The solvents may include water, $C_1$-$C_6$ alcohols (e.g., methanol, ethanol, or isopropanol), cyclic or acyclic ether solvents (e.g., diethyl ether, diisopropyl ether, tert-butyl methyl ether, or tetrahydrofuran), aromatic hydrocarbons (e.g., benzene, toluene, or xylene), aliphatic or alicyclic saturated hydrocarbons (e.g., hexane, heptane, or cyclohexane), polar aprotic solvents (e.g., acetonitrile, dimethyl formamide, or dimethyl sulfoxide), or mixtures thereof. In some embodiments, the preferred solvents may be water or $C_1$-$C_6$ alcohols.

The product 1 may be isolated and purified using methods known to those of skill in the art (e.g., extraction, filtration, distillation or crystallization).

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," "contain," "including," "includes," "include," and "have" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds) and provided literal support for and includes the end points of 10 and 100.

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. These broad, intermediate, and narrow numerical ranges should be applied not only to the specific values, but should also be applied to differences between these specific values.

EXAMPLES

The processes provided by the present invention are further illustrated by the following examples:

Example 1

3-Dimethylaminopropanol using dimethylamine hydrochloride

5% Palladium on carbon (42.6% in water; 350 mg; 7.5 wt % based on 3-hydroxypropionitrile) was added to a small Parr pressure bottle. 40% Dimethylamine in water (3.71 mL; 3.30 g; 29.3 mmol; 1.0 equiv) was added followed by 0.55 mL of water. Dimethylamine hydrochloride (0.60 g; 7.35 mmol; 0.25 equiv) was added followed by 3-hydroxypropionitrile (2.0 mL; 2.08 g; 29.3 mmol). The mixture was placed under 45 psig hydrogen and shaken for 4 hours, at which point $^1$H NMR (nuclear magnetic resonance) analysis indicated 94% conversion with >99.5% selectivity.

$^1$H NMR (CDCl$_3$) δ (ppm): 3.79 (t, 2H, J=5.2 Hz); 2.53 (t, 2H, J=5.9 Hz); 2.26 (s, 6H); 1.69 (m(5), 2H, J=5.5 Hz).

Comparative Example 1

3-Dimethylaminopropanol with no acid addition salt

5% Palladium on carbon (42.6% in water; 350 mg; 7.5 wt % based on 3-hydroxypropionitrile) was added to a small Parr pressure bottle. 40% Dimethylamine in water (4.63 mL; 4.12 g; 36.6 mmol; 1.25 equiv) was added followed by 3-hydroxypropionitrile (2.0 mL; 2.08 g; 29.3 mmol). The mixture was placed under 45 psig hydrogen and shaken for 4 hours, at which point $^1$H NMR analysis indicated 67% conversion.

TABLE 1

Reaction rate comparison

| Time | Example 1 | Comparative example 1 |
|---|---|---|
| 4 hours | 94% | 67% |

Comparative Example 2

3-Dimethylaminopropanol with no acid addition salt

5% Palladium on carbon (38.6% in water; 648 mg; 5 wt % based on 3-hydroxypropionitrile) was added to a Parr pressure bottle. 40% Dimethylamine in water (8.72 g; 77 mmol; 1.1 equiv) was added followed by 3-hydroxypropionitrile (5.0 g; 70.3 mmol). The mixture was placed under 45 psig hydrogen and shaken and the course of the reaction was followed by hydrogen uptake (pressure drop). The reaction was stopped after 20 h, at which point $^1$H NMR analysis indicated 95.9% conversion. Based on this data, the conversion after 1 h was 18.7%; after 2 h, 32.8%; after 3 h, 43.9%; after 4 h, 53.7%; after 5 h, 61.4%, after 6 h, 67.3%, after 8 h, 77.1%; after 10 h, 83.5%; after 12 h, 88.6%; after 14 h, 91.6%; after 16 h, 93.3%; and after 18 h, 95.0%.

Example 2

3-Dimethylaminopropanol using dimethylamine hydrochloride

5% Palladium on carbon (38.6% in water; 648 mg; 5 wt % based on 3-hydroxypropionitrile) was added to a Parr pressure bottle. 40% Dimethylamine in water (6.73 g; 59.8 mmol; 0.85 equiv) was added followed by dimethylamine hydrochloride (1.43 g; 17.6 mmol; 0.25 equiv) and 3-hydroxypropionitrile (5.0 g; 70.3 mmol). The mixture was placed under 45 psig hydrogen and shaken and the course of the reaction was followed by hydrogen uptake (pressure drop). The reaction was stopped after 12 h, at which point $^1$H NMR analysis indicated 98.7% conversion with >99.5% selectivity. Based on this data, the conversion after 1 h was 30.5%; after 2 h, 53.6%; after 3 h, 69.9%; after 4 h, 80.5%; after 5 h, 86.7%, after 6 h, 90.7%, after 8 h, 95.6%; and after 10 h, 98.3%.

Example 3

3-Dimethylaminopropanol using dimethylammonium acetate

5% Palladium on carbon (38.6% in water; 648 mg; 5 wt % based on 3-hydroxypropionitrile) was added to a Parr pressure bottle. 40% Dimethylamine in water (6.73 g; 59.8 mmol; 0.85 equiv) was added. A pre-prepared equimolar mixture of dimethylamine and acetic acid (60.9% in water; 3.04 g; 17.6 mmol; 0.25 equiv) was added followed by 3-hydroxypropionitrile (5.0 g; 70.3 mmol). The mixture was placed under 45 psig hydrogen and shaken and the course of the reaction was followed by hydrogen uptake (pressure drop). The reaction was stopped after 13 h, at which point $^1$H NMR analysis indicated 97.6% conversion with >99.5% selectivity. Based on this data, the conversion after 1 h was 23.1%; after 2 h, 40.9%; after 3 h, 55.5%; after 4 h, 66.8%; after 5 h, 75.3%, after 6 h, 81.4%, after 8 h, 89.5%; after 10 h, 94.0%; and after 12 h, 96.4%.

Example 4

3-Dimethylaminopropanol using sulfuric acid addition salt

40% Dimethylamine in water (4.63 mL; 4.12 g; 36.6 mmol; 1.25 equiv) was added to a small Parr pressure bottle which was cooled in ice-water. Sulfuric acid (0.195 mL; 0.359 g; 3.66 mmol; 0.125 equiv) was added slowly dropwise (exothermic). 5% Palladium on carbon (46.0% in water; 225 mg; 5 wt % based on 3-hydroxypropionitrile) was added followed by 3-hydroxypropionitrile (2.0 mL; 2.08 g; 29.3 mmol). The mixture was placed under 45 psig hydrogen and shaken for 3 hours, at which point $^1$H NMR analysis indicated 52.3% conversion with >99.5% selectivity.

TABLE 2

Dimethylamine addition salt comparison

| | Comparative example 2 | Example 2 | Example 3 | Example 4 |
|---|---|---|---|---|
| | | Addition salt | | |
| Time (h) | no acid salt | dimethylamine hydrochloride | dimethylammonium acetate | dimethylammonium sulfate |
| | | Conversion | | |
| 1 | 18.7% | 30.5% | 23.1% | ND |
| 2 | 32.8% | 53.6% | 40.9% | ND |
| 3 | 43.9% | 69.9% | 55.5% | 52.3% |
| 4 | 53.7% | 80.5% | 66.8% | ND |
| 5 | 61.4% | 86.7% | 75.3% | ND |
| 6 | 67.3% | 90.7% | 81.4% | ND |
| 8 | 77.1% | 95.6% | 89.5% | ND |
| 10 | 83.5% | 98.3% | 94.0% | ND |
| 12 | 88.6% | ND | 96.4% | ND |

ND: not determined

Comparative Example 3

3-Dimethylaminopropanol under basic conditions

50% Sodium hydroxide (0.585 g; 7.32 mmol; 0.25 equiv) was added to a small Parr pressure bottle. 40% Dimethylamine in water (4.63 mL; 4.12 g; 36.6 mmol; 1.25 equiv) was added followed by 3-hydroxypropionitrile (2.0 mL;

2.08 g; 29.3 mmol) and 5% palladium on carbon (46.0% in water; 226 mg; 5 wt % based on 3-hydroxypropionitrile). The mixture was placed under 45 psig hydrogen and shaken for 3 hours at ambient temperature, at which point $^1$H NMR analysis indicated 10% conversion.

Comparative Example 4

3-Dimethylaminopropanol with no acid addition salt and 5 wt % catalyst

5% Palladium on carbon (46.0% in water; 225 mg; 5 wt % based on 3-hydroxypropionitrile) was added to a small Parr pressure bottle. 40% Dimethylamine in water (4.63 mL; 4.12 g; 36.6 mmol; 1.25 equiv) was added followed by 3-hydroxypropionitrile (2.0 mL; 2.08 g; 29.3 mmol). The mixture was placed under 45 psig hydrogen and shaken for 3 hours, at which point $^1$H NMR analysis indicated 44.6% conversion.

Example 5

3-Dimethylaminopropanol using 0.25 equiv dimethylamine hydrochloride

5% Palladium on carbon (46.0% in water; 225 mg; 5 wt % based on 3-hydroxypropionitrile) was added to a small Parr pressure bottle. 40% Dimethylamine in water (3.71 mL; 3.30 g; 29.3 mmol; 1.0 equiv) was added followed by 0.55 mL of water. Dimethylamine hydrochloride (0.60 g; 7.35 mmol; 0.25 equiv) was added followed by 3-hydroxypropionitrile (2.0 mL; 2.08 g; 29.3 mmol). The mixture was placed under 45 psig hydrogen and shaken for 3 hours, at which point $^1$H NMR analysis indicated 72.4% conversion with >99.5% selectivity.

Example 6

3-Dimethylaminopropanol using 0.5 equiv dimethylamine hydrochloride

5% Palladium on carbon (46.0% in water; 225 mg; 5 wt % based on 3-hydroxypropionitrile) was added to a small Parr pressure bottle. 40% Dimethylamine in water (2.78 mL; 2.47 g; 21.95 mmol; 0.75 equiv) was added followed by 1.11 mL of water. Dimethylamine hydrochloride (1.19 g; 14.59 mmol; 0.50 equiv) was added followed by 3-hydroxypropionitrile (2.0 mL; 2.08 g; 29.3 mmol). The mixture was placed under 45 psig hydrogen and shaken for 3 hours, at which point $^1$H NMR analysis indicated 76.2% conversion with >99.5% selectivity.

Example 7

3-Dimethylaminopropanol using 0.625 equiv dimethylamine hydrochloride

5% Palladium on carbon (46.0% in water; 225 mg; 5 wt % based on 3-hydoxypropionitrile) added to a small Parr pressure bottle. 40% Dimethylamine in water (2.32 mL; 2.06 g; 18.29 mmol; 0.625 equiv) was added followed by 1.39 mL of water. Dimethylamine hydrochloride (1.49 g; 18.31 mmol; 0.625 equiv) was added followed by 3-hydroxypropionitrile (2.0 mL; 2.08 g; 29.3 mmol). The mixture was placed under 45 psig hydrogen and shaken for 3 hours, at which point $^1$H NMR analysis indicated 78.3% conversion with >99.5% selectivity.

Example 8

3-Dimethylaminopropanol using 1.0 equiv dimethylamine hydrochloride

5% Palladium on carbon (46.0% in water; 225 mg; 5 wt % based on 3-hydroxypropionitrile) was added to a small Parr pressure bottle. 40% Dimethylamine in water (0.93 mL; 0.83 g; 7.33 mmol; 0.25 equiv) was added followed by 2.22 mL of water. Dimethylamine hydrochloride (2.39 g; 29.3 mmol; 1.0 equiv) was added followed by 3-hydroxypropionitrile (2.0 mL; 2.08 g; 29.3 mmol). The mixture was placed under 45 psig hydrogen and shaken for 3 hours, at which point $^1$H NMR analysis indicated 77.7% conversion with >99.5% selectivity.

Example 9

3-Dimethylaminopropanol using 1.25 equiv dimethylamine hydrochloride and no amine 5% Palladium on carbon (46.0% in water; 225 mg; 5 wt % based on 3-hydroxypropionitrile) was added to a small Parr pressure bottle. Water (2.22 mL) was added. Dimethylamine hydrochloride (2.99 g; 36.63 mmol; 1.25 equiv) was added followed by 3-hydroxypropionitrile (2.0 mL; 2.08 g; 29.3 mmol). The mixture was placed under 45 psig hydrogen and shaken for 3 hours, at which point $^1$H NMR analysis indicated 71.3% conversion with >99.5% selectivity.

TABLE 3

Rate effect of varying amine to amine hydrochloride ratio

| | Comparative example 4 | Example 5 | Example 6 | Example 7 | Example 8 | Example 9 |
|---|---|---|---|---|---|---|
| Ratio amine:amine hydrochloride | 100:0 | 4:1 | 3:1 | 1:1 | 1:4 | 0:100 |
| Conversion at 3 hours | 44.6% | 72.4% | 76.2% | 78.3% | 77.7% | 71.3% |

Example 10

3-Dimethylaminopropanol using 0.25 equiv dimethylamine hydrochloride at ambient temperature 5% Palladium on carbon (38.6% in water; 972 mg; 7.5 wt % based on 3-hydroxypropionitrile) was added to a Parr pressure bottle. 40% Dimethylamine in water (6.74 g; 59.8 mmol; 0.85 equiv) was added followed by dimethylamine hydrochloride (1.43 g; 17.6 mmol; 0.25 equiv) and 3-hydroxypropionitrile (5.0 g; 70.3 mmol). The mixture was placed under 45 psig hydrogen and shaken at ambient temperature. The course of the reaction was followed by hydrogen uptake (pressure drop). The reaction was stopped after 6.58 h, at which point $^1$H NMR analysis indicated 99.4% conversion with >99.5% selectivity. Based on this data, the conversion after 1 h was 35.1%; after 2 h, 61.0%; after 3 h, 78.1%; after 4 h, 89.2%, after 5 h, 95.2%; and after 6 h, 98.0%.

Example 11

3-Dimethylaminopropanol using 0.25 equiv dimethylamine hydrochloride at 50° C.

5% Palladium on carbon (38.6% in water; 972 mg; 7.5 wt % based on 3-hydroxypropionitrile) was added to a Parr pressure bottle. 40% Dimethylamine in water (6.74 g; 59.8 mmol; 0.85 equiv) was added followed by dimethylamine hydrochloride (1.43 g; 17.6 mmol; 0.25 equiv) and 3-hydroxypropionitrile (5.0 g; 70.3 mmol). The mixture was placed under 45 psig hydrogen, heated to an internal temperature of 50° C., and shaken. The course of the reaction was followed by hydrogen uptake (pressure drop). The reaction was stopped after 4 h, at which point $^1$H NMR analysis indicated >99.9% conversion with >99.5% selectivity. Based on this data, the conversion after 1 h was 53.7%; after 2 h, 90.5%; after 3 h, 99.5%; and after 3.5 h, >99.9%.

Example 12

3-Dimethylaminopropanol using 0.25 equiv dimethylamine hydrochloride at 75° C.

5% Palladium on carbon (38.6% in water; 972 mg; 7.5 wt % based on 3-hydroxypropionitrile) was added to a Parr pressure bottle. 40% Dimethylamine in water (6.74 g; 59.8 mmol; 0.85 equiv) was added followed by dimethylamine hydrochloride (1.43 g; 17.6 mmol; 0.25 equiv) and 3-hydroxypropionitrile (5.0 g; 70.3 mmol). The mixture was placed under 45 psig hydrogen, heated to an internal temperature of 75° C. and shaken. The course of the reaction was followed by hydrogen uptake (pressure drop). The reaction was stopped after 4 h, at which point $^1$H NMR analysis indicated >99.9% conversion with 99.1% selectivity. Based on this data, the conversion after 1 h was 53.0%; after 2 h, 92.6%; after 3 h, 98.9%; and after 3.5 h, 99.4%.

TABLE 4

Rate effect of temperature

| Time (h) | Example 10 ambient temp | Example 11 50° C. conversion | Example 12 75° C. |
|---|---|---|---|
| 1 | 35.1% | 53.7% | 53.0% |
| 2 | 61.0% | 90.5% | 92.6% |
| 3 | 78.1% | 99.5% | 98.9% |
| 4 | 89.2% | >99.9% | >99.9% |

Example 13

3-Dimethylaminopropanol with isolation and purification

5% Palladium on carbon (46% in water; 2.26 g; 5 wt % based on 3-hydroxypropionitrile) was added to a Parr pressure bottle. 40% Dimethylamine in water (33.0 g; 293 mmol; 1.0 equiv) was added followed by dimethylamine hydrochloride (5.97 g; 73.2 mmol; 0.25 equiv) and 3-hydroxypropionitrile (20.80 g; 293 mmol). The mixture was placed under 45 psig hydrogen and shaken at ambient temperature. The course of the reaction was followed by hydrogen uptake, which had virtually ceased after 12.5 h (99% conversion by hydrogen uptake). The reaction was stopped after 22.5 h, and $^1$H NMR analysis indicated >99.9% conversion. The mixture was treated with 50% sodium hydroxide (5.85 g; 73.2 mmol; 0.25 equiv) and filtered through filter paper, and the filtrate was set aside. The Parr pressure bottle and the catalyst cake were washed with water to afford 61.04 g of wash, which was analyzed by $^1$H NMR to contain 4.6 wt % 3-dimethylaminopropanol (2.81 g). The initial filtrate was treated with 50 mL of cyclohexane, a Dean-Stark trap was attached, and the water was removed by atmospheric azeotropic distillation until no more water distilled overhead. The remaining cyclohexane was removed by distillation, and the remainder was distilled under reduced pressure (12 mm Hg) to afford 25.56 g of 3-dimethylaminopropanol (93% yield based on the theoretical yield less the amount in the wash) which was >99% pure by $^1$H NMR.

Example 14

3-Dimethylaminopropanol using 2% Palladium on alumina

2% Palladium on alumina (260 mg; 12.5 wt % based on 3-hydroxypropionitrile) was added to a small Parr pressure bottle. 40% Dimethylamine in water (2.32 mL; 2.06 g; 18.29 mmol; 0.625 equiv) was added followed by 1.39 mL of water. Dimethylamine hydrochloride (1.49 g; 18.31 mmol; 0.625 equiv) was added followed by 3-hydroxypropionitrile (2.0 mL; 2.08 g; 29.3 mmol). The mixture was placed under 45 psig hydrogen and shaken for 3 hours, at which point $^1$H NMR analysis indicated 34.6% conversion.

Example 15

3-Dimethylaminopropanol using 5% Palladium on alumina with dimethylamine hydrochloride 5% Palladium on alumina (375 mg; 7.5 wt % based on 3-hydroxypropionitrile) was added to a small Parr pressure bottle. 40% Dimethylamine in water (6.74 g; 59.8 mmol; 0.85 equiv) was added followed by dimethylamine hydrochloride (1.43 g; 17.6 mmol; 0.25 equiv). 3-Hydroxypropionitrile (5.00 g; 70.3 mmol) was then added. The mixture was placed under 45 psig hydrogen and shaken at ambient temperature. The course of the reaction was followed by hydrogen uptake (pressure drop). The reaction was stopped after 8.5 h, at which point $^1$H NMR analysis indicated 75% conversion. Based on this data, the conversion after 1 h was 8.9%; after 2 h, 17.7%; after 3 h, 26.5%; after 4 h, 36.4%; after 5 h, 46.2%, after 6 h, 55.0%, after 7 h, 63.9%; and after 8 h, 71.3%.

Comparative Example 5

3-Dimethylaminopropanol using 5% Palladium on alumina with no acid addition salt 5% Palladium on alumina (375 mg; 7.5 wt % based on 3-hydroxypropionitrile) was added to a small Parr pressure bottle. 40% Dimethylamine in water (8.72 g; 77.4 mmol; 1.1 equiv) was added followed by 3-hydroxypropionitrile (5.00 g; 70.3 mmol). The mixture was placed under 45 psig hydrogen and shaken at ambient temperature. The course of the reaction was followed by hydrogen uptake (pressure drop). The reaction was stopped after 8.3 h, at which point ¹H NMR analysis indicated 49% conversion. Based on this data, the conversion after 1 h was 6.7%; after 2 h, 13.4%; after 3 h, 20.6%; after 4 h, 27.4%; after 5 h, 34.1%, after 6 h, 39.2%, after 7 h, 43.9%; and after 8 h, 47.5%.

TABLE 5

Acid addition salt comparison with palladium on alumina

| Time (h) | Example 15 Amine hydrochloride Conversion | Comparative Example 5 No acid addition salt |
|---|---|---|
| 1 | 8.9% | 6.7% |
| 2 | 17.7% | 13.4% |
| 3 | 26.5% | 20.6% |
| 4 | 36.4% | 27.4% |
| 5 | 46.2% | 34.1% |
| 6 | 55.0% | 39.2% |
| 7 | 63.9% | 43.9% |
| 8 | 71.3% | 47.5% |

Example 16

3-Dimethylaminopropanol using 5% Platinum on carbon with dimethylamine hydrochloride 5% Platinum on carbon (36.5% in water; 684 mg; 5 wt % based on 3-hydroxypropionitrile) was added to a Parr pressure bottle. 40% Dimethylamine in water (6.74 g; 59.8 mmol; 0.85 equiv) was added followed by dimethylamine hydrochloride (1.43 g; 17.6 mmol; 0.25 equiv) and 3-hydroxypropionitrile (5.0 g; 70.3 mmol). The mixture was placed under 45 psig hydrogen and shaken at ambient temperature. The course of the reaction was followed by hydrogen uptake (pressure drop). The reaction was stopped after 7.375 h, at which point ¹H NMR analysis indicated 13.4% conversion. Based on this data, the conversion after 1 h was 1.3%; after 2 h, 2.7%; after 3 h, 4.0%; after 4 h, 6.6%; after 5 h, 8.9%, after 6 h, 10.7%, and after 7 h, 13.0%.

Comparative Example 6

3-Dimethylaminopropanol using 5% Platinum on carbon with no acid addition salt

5% Platinum on carbon (36.5% in water; 684 mg; 5 wt % based on 3-hydroxypropionitrile) was added to a Parr pressure bottle. 40% Dimethylamine in water (8.72 g; 77.4 mmol; 1.1 equiv) was added followed by 3-hydroxypropionitrile (5.0 g; 70.3 mmol). The mixture was placed under 45 psig hydrogen and shaken at ambient temperature. The course of the reaction was followed by hydrogen uptake (pressure drop). The reaction was stopped after 5.8 h, at which point ¹H NMR analysis indicated 7.0% conversion. Based on this data, the conversion after 1 h was 0.9%; after 2 h, 1.3%; after 3 h, 3.1%; after 4 h, 4.4%; and after 5 h, 6.1.

TABLE 6

Acid addition salt comparison with platinum on carbon

| Time (h) | Example 16 Amine hydrochloride Conversion | Comparative Example 6 No acid addition salt |
|---|---|---|
| 1 | 1.3% | 0.9% |
| 2 | 2.7% | 1.3% |
| 3 | 4.0% | 3.1% |
| 4 | 6.6% | 4.4% |
| 5 | 8.9% | 6.1% |

Comparative Example 7

3-Dimethylaminopropanol using Amberlyst 36 solid heterogeneous acid

5% Palladium on carbon (38.6% in water; 972 mg; 7.5 wt % based on 3-hydroxypropionitrile) was added to a Parr pressure bottle. 40% Dimethylamine in water (9.91 g; 88 mmol; 1.25 equiv) was added followed by Amberlyst 36 sulfonic acid resin (3.25 g; 17.6 meq acid; 0.25 equiv) and 3-hydroxypropionitrile (5.0 g; 70.3 mmol). The mixture was placed under 45 psig hydrogen and shaken at ambient temperature. The course of the reaction was followed by hydrogen uptake (pressure drop). The reaction was stopped after 6.75 h, at which point ¹H NMR analysis indicated 43.8% conversion. Based on this data, the conversion after 1 h was 15.8%; after 2 h, 24.6%; after 3 h, 31.0%; after 4 h, 35.5%; after 5 h, 38.9%; and after 6 h, 42.3%.

Comparative Example 8

3-Dimethylaminopropanol using Amberlyst 15 solid heterogeneous acid

5% Palladium on carbon (38.6% in water; 972 mg; 7.5 wt % based on 3-hydroxypropionitrile) was added to a Parr pressure bottle. 40% Dimethylamine in water (9.91 g; 88 mmol; 1.25 equiv) was added followed by Amberlyst 15 sulfonic acid resin (3.74 g; 17.6 meq acid; 0.25 equiv) and 3-hydroxypropionitrile (5.0 g; 70.3 mmol). The mixture was placed under 45 psig hydrogen and shaken at ambient temperature. The course of the reaction was followed by hydrogen uptake (pressure drop). The reaction was stopped after 5.83 h, at which point ¹H NMR analysis indicated 31.5% conversion. Based on this data, the conversion after 1 h was 13.7%; after 2 h, 20.0%; after 3 h, 24.2%; after 4 h, 27.8%; and after 5 h, 29.9%.

Comparative Example 9

3-Dimethylaminopropanol using 7.5 wt % Pd/C with no acid

5% Palladium on carbon (38.6% in water; 972 mg; 7.5 wt % based on 3-hydroxypropionitrile) was added to a Parr pressure bottle. 40% Dimethylamine in water (9.91 g; 88 mmol; 1.25 equiv) was added followed by 3-hydroxypropionitrile (5.0 g; 70.3 mmol). The mixture was placed under 45 psig hydrogen and shaken at ambient temperature. The course of the reaction was followed by hydrogen uptake (pressure drop). The reaction was stopped after 7.4 h, at which point ¹H NMR analysis indicated 79.4% conversion. Based on this data, the conversion after 1 h was 22.1%; after 2 h, 37.7%; after 3 h, 50.0%; after 4 h, 59.3%; after 5 h, 66.6%; after 6 h, 72.5%; and after 7 h, 77.4%.

TABLE 7

Effect of heterogenous solid acids

| Time (h) | Example 10 Amine hydrochloride | Comparative Example 9 No acid addition salt | Comparative Example 7 Amberlyst 36 | Comparative Example 6 Amberlyst 15 |
|---|---|---|---|---|
| | | | Conversion | |
| 1 | 35.1% | 22.1% | 15.8% | 13.7% |
| 2 | 61.0% | 37.7% | 24.6% | 20.0% |
| 3 | 78.1% | 50.0% | 31.0% | 24.2% |
| 4 | 89.2% | 59.3% | 35.5% | 27.8% |
| 5 | 95.2% | 66.6% | 38.9% | 29.9% |
| 6 | 98.0% | 72.5% | 42.3% | ND |

Comparative Example 10

3-Diethylaminopropanol with diethylamine hydrochloride

5% Palladium on carbon (49.5% in water; 218 mg; 5 wt % based on 3-hydroxypropionitrile) was added to a Parr pressure bottle. Water (3.21 g) was added followed by diethylamine (2.14 g; 29.3 mmol; 1.0 equiv). Diethylamine hydrochloride (0.802 g; 7.32 mmol; 0.25 equiv) was added followed by 3-hydroxypropionitrile (2.08 g; 29.3 mmol). The mixture was placed under 45 psig hydrogen and shaken at ambient temperature. The reaction was stopped after 4 h and sampled and analyzed by $^1$H NMR to indicate 69% conversion.

$^1$H NMR (DMSO-d$_6$) δ (ppm): 3.45 (t, 2H, J=6.3 Hz); 2.50 (t, 2H, J=7.4 Hz); 2.44 (q, 4H, J=7.2 Hz); 1.54 (m(5), 2H, J=6.3 Hz); 0.95 (t, 6H, J=7.1 Hz).

Comparative Example 11

3-Diethylaminopropanol with no acid addition salt

5% Palladium on carbon (49.5% in water; 218 mg; 5 wt % based on 3-hydroxypropionitrile) was added to a Parr pressure bottle. Water (3.21 g) was added followed by diethylamine (2.68 g; 36.6 mmol; 1.25 equiv) and 3-hydroxypropionitrile (2.08 g; 29.3 mmol). The mixture was placed under 45 psig hydrogen and shaken at ambient temperature. The reaction was stopped after 4 h and sampled and analyzed by $^1$H NMR to indicate 72% conversion.

TABLE 8

Effect of acid addition salt with diethylamine

| | Comparative Example 10 Amine hydrochloride | Comparative Example 11 No acid addition salt |
|---|---|---|
| Conversion at 4 hours | 69% | 72% |

Example 17 n-Propyl dimethylamine with dimethylamine hydrochloride

5% Palladium on carbon (38.6% in water; 972 mg; 9.7 wt % based on propionitrile) was added to a Parr pressure bottle. 40% Dimethylamine in water (6.73 g; 59.8 mmol; 0.85 equiv) was added followed by dimethylamine hydrochoride (1.43 g; 17.6 mmol; 0.25 equiv) and propionitrile (3.87 g; 70.3 mmol). The mixture was placed under 45 psig hydrogen and shaken at ambient temperature. The course of the reaction was followed by hydrogen uptake (pressure drop). The reaction was stopped after 7.17 h, at which point $^1$H NMR analysis indicated 90.0% conversion to n-propyl dimethylamine. Based on this data, the conversion after 1 h was 19.3%; after 2 h, 35.4%; after 3 h, 50.4%; after 4 h, 63.8%; after 5 h, 74.5%; after 6 h, 83.6%; and after 7 h, 89.5%.

$^1$H NMR (DMSO-d$_6$) δ (ppm): 2.11 (t, 2H, J=7.2 Hz); 2.07 (s, 6H); 1.37 (m(6), 2H, J=7.5 Hz); 0.81 (t, 3H, J=7.4 Hz).

Comparative Example 12 n-Propyl dimethylamine with no acid addition salt

5% Palladium on carbon (38.6% in water; 972 mg; 9.7 wt % based on propionitrile) was added to a Parr pressure bottle. 40% Dimethylamine in water (8.72 g; 77.4 mmol; 1.1 equiv) was added followed by propionitrile (3.87 g; 70.3 mmol). The mixture was placed under 45 psig hydrogen and shaken at ambient temperature. The course of the reaction was followed by hydrogen uptake (pressure drop). The reaction was stopped after 6.25 h, at which point $^1$H NMR analysis indicated 40.0% conversion to n-propyl dimethylamine. Based on this data, the conversion after 1 h was 10.4%; after 2 h, 17.3%; after 3 h, 23.7%; after 4 h, 29.6%; after 5 h, 34.6%; and after 6 h, 39.0%.

TABLE 9

Effect of acid addition salt with propionitrile

| Time (h) | Example 17 Amine hydrochloride | Comparative Example 12 No acid addition salt |
|---|---|---|
| | Conversion | |
| 1 | 19.3% | 10.4% |
| 2 | 35.4% | 17.3% |
| 3 | 50.4% | 23.7% |
| 4 | 63.8% | 29.6% |
| 5 | 74.5% | 34.6% |
| 6 | 83.6% | 39.0% |

Example 18

Tetramethyl 1,3-propylenediamine with dimethylamine hydrochloride

5% Palladium on carbon (38.6% in water; 972 mg; 5.4 wt % based on 3-dimethylaminopropionitrile) was added to a Parr pressure bottle. 40% Dimethylamine in water (6.73 g; 59.8 mmol; 0.85 equiv) was added followed by dimethylamine hydrochoride (1.43 g; 17.6 mmol; 0.25 equiv) and 3-dimethylaminopropionitrile (6.90 g; 70.3 mmol). The mixture was placed under 45 psig hydrogen and shaken at ambient temperature. The course of the reaction was followed by hydrogen uptake (pressure drop). The reaction was stopped after 7.3 h, at which point $^1$H NMR analysis indicated 86% conversion to tetramethyl 1,3-propylenediamine with 93% selectivity. Based on this data, the conversion after 1 h was 28.3%; after 2 h, 47.8%; after 3 h, 60.7%; after 4 h, 70.0%; after 5 h, 76.7%; after 6 h, 81.6%; and after 7 h, 85.6%.

$^1$H NMR (DMSO-d$_6$) δ (ppm): 2.16 (t, 4H, J=7.2 Hz); 2.08 (s, 12H); 1.48 (m(5), 2H, J=7.1 Hz).

Comparative Example 13

Tetramethyl 1,3-propylenediamine with no acid addition salt

5% Palladium on carbon (38.6% in water; 972 mg; 5.4 wt % based on 3-dimethylaminopropionitrile) was added to a Parr pressure bottle. 40% Dimethylamine in water (8.72 g; 77.4 mmol; 1.1 equiv) was added followed by 3-dimethylaminopropionitrile (6.90 g; 70.3 mmol). The mixture was placed under 45 psig hydrogen and shaken at ambient temperature. The course of the reaction was followed by hydrogen uptake (pressure drop). The reaction was stopped after 6.42 h, at which point $^1$H NMR analysis indicated 60% conversion to tetramethyl 1,3-propylenediamine with 94% selectivity. Based on this data, the conversion after 1 h was 22.4%; after 2 h, 33.3%; after 3 h, 41.5%; after 4 h, 48.0%; after 5 h, 54.0%; and after 6 h, 58.4%.

TABLE 10

Effect of acid addition salt with 3-dimethylaminopropionitrile

| Time (h) | Example 18 Amine hydrochloride | Comparative Example 13 No acid addition salt |
|---|---|---|
| | Conversion | |
| 1 | 28.3% | 22.4% |
| 2 | 47.8% | 33.3% |
| 3 | 60.7% | 41.5% |
| 4 | 70.0% | 48.0% |
| 5 | 76.7% | 54.0% |
| 6 | 81.6% | 58.4% |

Example 19

N,N-Dimethylbenzylamine with dimethylamine hydrochloride

Isopropanol (7.5 g) was added to a Parr pressure bottle followed by 5% palladium on carbon (38.6% in water; 972 mg; 5.2 wt % based on benzonitrile). 40% Dimethylamine in water (6.73 g; 59.8 mmol; 0.85 equiv) was added followed by dimethylamine hydrochoride (1.43 g; 17.6 mmol; 0.25 equiv) and benzonitrile (7.25 g; 70.3 mmol). The mixture was placed under 45 psig hydrogen and shaken at ambient temperature. The course of the reaction was followed by hydrogen uptake (pressure drop). The reaction was stopped after 8.25 h, at which point $^1$H NMR analysis indicated 68% conversion to N,N-dimethylbenzylamine. Based on this data, the conversion after 1 h was 45.5%; after 2 h, 55.0%; after 3 h, 59.0%; after 4 h, 62.0%; after 5 h, 64.5%; after 6 h, 66.0%; after 7 h, 67.5%; and after 8 h, 68.0%.

$^1$H NMR (DMSO-d$_6$) δ (ppm): 7.35-7.15 (m, 5H); 3.65 (s, 2H); 2.28 (s, 6H).

Comparative Example 14

N,N-Dimethylbenzylamine with no acid addition salt

Isopropanol (7.5 g) was added to a Parr pressure bottle followed by 5% palladium on carbon (38.6% in water; 972 mg; 5.2 wt % based on benzonitrile). 40% Dimethylamine in water (8.72 g; 77.4 mmol; 1.1 equiv) was added followed by benzonitrile (7.25 g; 70.3 mmol). The mixture was placed under 45 psig hydrogen and shaken at ambient temperature. The course of the reaction was followed by hydrogen uptake (pressure drop). The reaction was stopped after 8 h, at which point $^1$H NMR analysis indicated 44% conversion to N,N-dimethylbenzylamine. Based on this data, the conversion after 1 h was 32.0%; after 2 h, 36.1%; after 3 h, 38.2%; after 4 h, 40.3%; after 5 h, 42.4%; after 6 h, 43.5%; and after 7 h, 43.5%.

TABLE 11

Effect of acid addition salt with 3-dimethylaminopropionitrile

| Time (h) | Example 19 Amine hydrochloride | Comparative Example 14 No acid addition salt |
|---|---|---|
| | Conversion | |
| 1 | 45.5% | 32.0% |
| 2 | 55.0% | 36.1% |
| 3 | 59.0% | 38.2% |
| 4 | 62.0% | 40.3% |
| 5 | 64.5% | 42.4% |
| 6 | 66.0% | 43.5% |
| 7 | 67.5% | 43.5% |
| 8 | 68.0% | 44.0% |

Although the disclosure describes embodiments having specific structural features and/or methodological acts, it is to be understood that the claims are not necessarily limited to the specific features or acts described. Rather, the specific features and acts are merely illustrative some embodiments that fall within the scope of the claims of the disclosure.

What is claimed is:

1. A process for preparing a tertiary dimethylamine of the general formula (1):

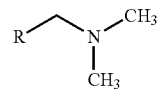

comprising reacting a nitrile of formula (2)

   2, dimethylamine, and a dimethylammonium acid addition salt in the presence of a catalyst and a hydrogen atmosphere, wherein R is an unsubstituted or substituted $C_1$-$C_{22}$ alkyl, wherein the $C_1$-$C_{22}$ alkyl group is straight or branched, an unsubstituted or substituted $C_3$-$C_8$cycloalkyl, an unsubstituted or substituted $C_6$-$C_{20}$ carbocyclic aryl, or an unsubstituted or substituted $C_1$-$C_{20}$ heterocyclic wherein the heteroatoms in the heterocyclic group are selected from sulfur, nitrogen, and oxygen, or mixtures thereof, wherein the dimethylammonium acid addition salt is present in an amount from about 0.01 to about 20 equivalents based on nitrile 2.

2. The process as recited in claim 1, wherein the $C_1$-$C_{22}$ alkyl group is substituted with one to three groups selected from a group consisting of a $C_1$-$C_6$ alkoxy, a $C_2$-$C_6$ alkoxycarbonyl, a $C_2$-$C_6$ alkanoyloxy, a hydroxyl, a carbocyclic aryl, and a heterocyclic.

3. The process as recited in claim 1, the $C_6$-$C_{20}$ carbocyclic aryl is:
a phenyl, a naphthyl, or an anthracenyl; or
a phenyl, a naphthyl, or an anthracenyl substituted with one to three substituents selected from a $C_1$-$C_6$ alkyl, a substituted $C_1$-$C_6$ alkyl, a hydroxy, a $C_2$-$C_{10}$ dialkylamino, a $C_6$-$C_{10}$ aryl, a substituted $C_6$-$C_{10}$ aryl, a $C_1$-$C_6$ alkoxy, a halogen, a carboxy, a $C_1$-$C_6$ alkanoyloxy, a $C_1$-$C_6$ alkylsulfonyl, a trifluoromethyl, a $C_2$-$C_6$ alkoxycarbonyl, or a $C_2$-$C_6$ alkanoylamino.

4. The process as recited in claim 1, wherein the $C_3$-$C_8$ cycloalkyl is a saturated, carbocyclic hydrocarbon radical having three to eight carbon atoms and is substituted with one to three groups selected from a group consisting of a $C_1$-$C_6$ alkoxy, a $C_2$-$C_6$ alkoxycarbonyl, a $C_2$-$C_6$ alkanoyloxy, a hydroxy, a $C_2$-$C_{10}$ dialkylamino, a carbocyclic aryl, and a heterocyclic.

5. The process as recited in claim 1, wherein the $C_1$-$C_{20}$ heterocyclic is a 5- or 6- membered aromatic ring containing one to four heteroatoms selected from oxygen, sulfur and nitrogen.

6. The process as recited in claim 1, wherein the $C_1$-$C_{20}$ heterocyclic is a thienyl, a fury, a pyrrolyl, an imidazolyl, a pyrazolyl, a thiazolyl, an isothiazolyl, an oxazolyl, an isoxazolyl, a triazolyl, a thiadiazolyl, an oxadiazolyl, a tetrazolyl, a pyridyl, a pyrimidyl, a benzoxazolyl, a benzothiazolyl, a benzimidazolyl, or an indolyl.

7. The process as recited in claim 1, wherein the $C_1$-$C_{20}$ heterocyclic is substituted with up to three groups from a group consisting of a $C_1$-$C_6$ alkyl, a $C_1$-$C_6$ alkoxy, a substituted $C_1$-$C_6$ alkyl, a hydroxy, a $C_2$-$C_{10}$ dialkylamino, an aryl, aryloxy, a $C_2$-$C_6$ alkoxycarbonyl, or a $C_2$-$C_6$ alkanoylamino.

8. The process as recited in claim 1, wherein the $C_1$-$C_{20}$ heterocyclic is substituted with a fused ring system which may be unsubstituted or substituted.

9. The process as recited in claim 1, wherein the process is carried out at a temperature from about −100° C. to about 200° C.

10. The process as recited in claim 1, wherein the catalyst is a Group VIII metal including one of palladium or platinum.

11. The process as recited in claim 1, wherein the process is carried out under a pressure from about 1 atmosphere to about 150 atmospheres (from about 0.1 to about 15.2 MPa).

12. The process as recited in claim 1, wherein an amount of dimethylamine present in the process comprises from about 0 to about 20 equivalents based on nitrile 2.

13. A process for the preparation of a tertiary dimethylamine represented by the formula (1):

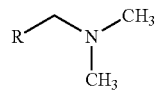

comprising reacting a nitrile of formula (2)

R—CN 2, dimethylamine, and dimethylammonium acid addition salt in the presence of a catalyst, wherein R is one or more of the following: a $C_1$-$C_{22}$ alkyl, a hydroxy-substituted $C_1$-$C_{22}$ alkyl, a dialkylamino-substituted $C_1$-$C_{22}$ alkyl, a carbocyclic aryl, and a substituted carbocyclic aryl group,
wherein the dimethylammonium acid addition salt is present in an amount from about 0.01 to about 20 equivalents based on nitrile 2.

14. The process as recited in claim 13, wherein the amination is carried out under an atmosphere containing hydrogen, wherein a pressure of the atmosphere is less than about 150 atmospheres (about 15.2 MPa).

15. The process as recited in claim 13, wherein an amount of dimethylamine present in the process comprises from about 0 to about 20 equivalents based on nitrile 2.

16. The process as recited in claim 13, wherein the dimethylamine is an aqueous solution with a dimethylamine content from about 10% to about 90%.

17. The process as recited in claim 13, wherein the dimethylammonium acid addition salt is obtained in situ by reacting dimethylamine with an acid, wherein the acid is a protic acid with a pKa of less than 5.

18. The process as recited in claim 17, wherein the acid is selected from one or more of the following: acetic acid, benzoic acid, propionic acid, hydrochloric acid, sulfuric acid, methanesulfonic acid, phosphoric acid, formic acid, and citric acid.

19. The process as recited in claim 13, wherein the dimethylammonium acid addition salt comprises one or more of the following: dimethylammonium acetate, dimethylammonium chloride, and dimethylammonium sulfate.

20. The process as recited in claim 13, wherein the process is carried out at a temperature from about −100° C. to about 200° C.

21. The process as recited in claim 13, wherein R is ethyl, 2-hydroxyethyl, 2-dimethylaminoethyl, phenyl or any combination thereof.

22. A process for the preparation of a tertiary dimethylamine represented by the formula (1):

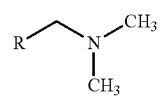

comprising reacting a nitrile of formula (2)

R—CN 2, dimethylamine, and an acid in the presence of a catalyst, wherein the acid is a protic acid with a pKa of less than 5, and wherein R is one or more of the following: a $C_1$-$C_{22}$ alkyl, a hydroxy-substituted $C_1$-$C_{22}$ alkyl, a dialkylamino-substituted $C_1$-$C_{22}$ alkyl, a carbocyclic aryl, and a substituted carbocyclic aryl group.

23. The process as recited in claim 22, wherein the reacting is carried out under an atmosphere containing hydrogen, wherein a pressure of the atmosphere is less than about 150 atmospheres (about 15.2 MPa).

24. The process as recited in claim 22, wherein an amount of dimethylamine present in the process comprises from about 0 to about 20 equivalents based on nitrile 2.

25. The process as recited in claim 22, wherein the dimethylamine is an aqueous solution with a dimethylamine content from about 10% to about 90%.

26. The process as recited in claim 21, wherein the reacting is carried out at a temperature from about −100° C. to about 200° C.

27. The process as recited in claim 21, wherein R is ethyl, 2-hydroxyethyl, 2-dimethylaminoethyl, phenyl or any combination thereof.

28. The process as recited in claim 21, wherein the acid is selected from one or more of the following: acetic acid, benzoic acid, propionic acid, hydrochloric acid, sulfuric acid, methanesulfonic acid, phosphoric acid, formic acid, and citric acid.

* * * * *